United States Patent [19]

Carter et al.

[11] Patent Number: 5,332,745

[45] Date of Patent: Jul. 26, 1994

[54] TETRAHYDROPYRIMIDINE DERIVATIVES

[75] Inventors: Paul A. Carter; Nicholas J. Daniels, both of Sittingbourne; Steven J. Tapp, Faversham, all of England

[73] Assignee: Shell Research Limited, United Kingdom

[21] Appl. No.: 47,377

[22] Filed: Apr. 19, 1993

Related U.S. Application Data

[63] Continuation of Ser. No. 727,049, Jul. 9, 1991, abandoned.

[30] Foreign Application Priority Data

Jul. 31, 1990 [GB] United Kingdom ............ 9016800.6

[51] Int. Cl.$^5$ .................. A61K 31/505; C07D 239/12
[52] U.S. Cl. .................... 514/275; 544/330; 544/332
[58] Field of Search ............... 544/330, 332; 514/275

[56] References Cited

U.S. PATENT DOCUMENTS

| | | | |
|---|---|---|---|
| 4,374,143 | 2/1983 | Dolman et al. | 544/226 |
| 4,379,926 | 4/1983 | Gauthier et al. | 544/242 |
| 4,396,617 | 8/1983 | Dolman et al. | 544/226 |

FOREIGN PATENT DOCUMENTS

| | | | |
|---|---|---|---|
| 0155597 | 8/1951 | Australia | 544/242 |
| 0740936 | 11/1955 | United Kingdom | 544/242 |
| 2038305 | 7/1980 | United Kingdom | |

*Primary Examiner*—Mukund J. Shah
*Assistant Examiner*—Y. N. Gupta

[57] ABSTRACT

The invention provides a fungicidal composition comprising a carrier and, as active ingredient, certain tetrahydropyrimidine derivatives of the general formula

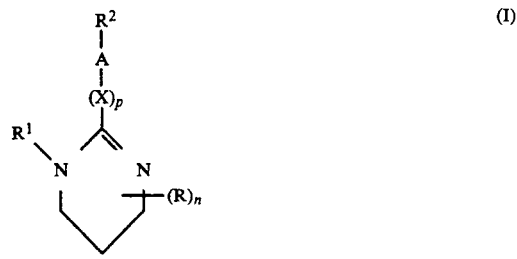

(I)

or an acid-addition salt or metal salt complex thereof, in which n is 0, 1, 2 or 3; R represents an optionally substituted alkyl, aryl or aralkyl group; $R^1$ represents a hydrogen atom or an optionally substituted alkyl or aralkyl group; $R^2$ represents an optionally substituted aryl group; p is 0 or 1; X represents a group —$NR^3$— or —$NR^3$—$NR^3$— where each $R^3$ independently represents a hydrogen atom or an optionally substituted alkyl, aryl or aralkyl group or $R^1$ and $(X)_p$—A—$R^2$ together represent a group —$(CR^4R^5)_q$—N(A—$R^2$)— where q is 2 or 3 and each of $R^4$ and $R^5$ is independently selected from a group consisting of hydrogen atoms and optionally substituted alkyl groups; and A represents a group—$(CR^6R^7)_m$—where m is 0, 1, 2, 3 or 4 and each of $R^6$ and $R^7$ is independently selected from a group consisting of hydrogen atoms and optionally substituted alkyl groups.

10 Claims, No Drawings

TETRAHYDROPYRIMIDINE DERIVATIVES

This application is a continuation of application Ser. No. 07/727,049, filed Jul. 9, 1991, now abandoned.

The present invention relates to certain tetrahydropyrimidine derivatives, some of which are novel, a process for their preparation, compositions containing such compounds and their use as fungicides.

NL 7711390 discloses compounds of the formula

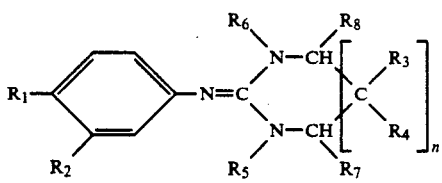

in which n is 0 or 1; $R_1$ and $R_2$ are the same or different and represent hydrogen, $C_{4-12}$ alkyl, $C_{4-12}$ cycloalkyl, $C_{4-12}$ alkoxy, $C_{4-12}$ alkylthio, phenylthio optionally substituted by halogen or $C_{1-4}$ alkyl, $C_{7-11}$ phenylalkyl, di($C_{2-6}$ alkyl)amino or $C_{4-12}$alkoxycarbonyl or $R_1$ and $R_2$ together may represent trimethylene, tetramethylene or butadienylene, with the proviso that $R_1$ and $R_2$ are not both hydrogen; $R_3$, $R_4$, $R_7$ and $R_8$ are the same or different and represent hydrogen or $C_{1-4}$ alkyl; and $R_5$ and $R_6$ are the same or different and represent hydrogen, $C_{1-4}$ alkyl or $C_{2-5}$ alkanoyl. Some of these compounds are shown to exhibit activity against certain phytopathogenic fungi.

DE 2941658 discloses compounds of formula (A) above in which n is 0 or 1; $R_1$ is an optionally halogenated $C_{3-12}$ alkyl, $C_{3-12}$ alkenyl, $C_{3-12}$ alkoxy, $C_{3-12}$ alkenyloxy, $C_{3-12}$ alkylthio, $C_{3-12}$ alkenylthio, $C_{3-12}$ alkoxyalkyl or $C_{3-12}$ alkylthioalkyl group, a $C_{3-12}$ mono-, bi- or tricycloalkyl group, a phenyl, phenoxy, phenylthio, $C_{6-10}$ phenylalkyl, $C_{6-10}$ phenylalkoxy, $C_{6-10}$ phenylalkenyl, $C_{6-10}$ phenylthioalkyl or $C_{6-10}$ phenylalkylthio group in which the phenyl group is optionally substituted by halogen or by optionally halogenated $C_{1-6}$alkyl, $C_{1-6}$alkoxy or $C_{1-6}$alkylthio, or a $C_{5-8}$furylalkyl or $C_{5-8}$ thienylalkyl group; $R_2$ is hydrogen or halogen; or $R_1$ and $R_2$ together represent tri- or tetramethylene; $R_3$ and $R_4$ are both hydrogen; $R_5$ and $R_6$ are hydrogen, $C_{1-4}$ alkyl or $C_{1-4}$ alkanoyl; $R_7$ is hydrogen or $C_{1-4}$ alkyl and $R_8$ is hydrogen. Certain of these compounds, some of which are also disclosed in NL 7711390, are shown to exhibit activity as plant growth regulators.

It has now been discovered that certain tetrahydropyrimidine derivatives exhibit exceptional activity against certain phytopathogenic fungi, particularly cereal diseases and, especially, powdery mildews.

According to the present invention there is therefore provided a fungicidal composition which comprises a carrier and, as active ingredient, a compound of the general formula

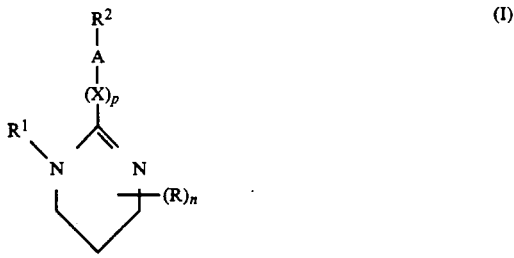

or an acid-addition salt or metal salt complex thereof, in which n is 0, 1, 2 or 3; R represents an optionally substituted alkyl, aryl or aralkyl group; $R^1$ represents a hydrogen atom or an optionally substituted alkyl or aralkyl group; $R^2$ represents an optionally substituted aryl group; p is 0 or 1; X independently represents a hydrogen atom or an optionally substituted alkyl, aryl or aralkyl group or represents a group —$NR^3$— or —$NR^3$—$NR^3$— where each $R^3$ independently represents a hydrogen atom or an optionally substituted alkyl, aryl or aralkyl group or $R^1$and $(X)_p$—A—$R^2$ together represent a group $(CR^4R^5)_q$—$N(A$—$R^2)$— where q is 2 or 3 and each of $R^4$ and $R^5$ is independently selected from a group consisting of hydrogen atoms and optionally substituted alkyl groups; and A represents a group —$(CR^6R^7)_m$— where m is 0, 1, 2, 3 or 4 and each of $R^6$ and $R^7$ is independently selected from a group consisting of hydrogen atoms and optionally substituted alkyl groups; with the provisos that
  (i) when p is 1, X is NH, m is 0, $R^1$ is H and n is 0 then $R^2$ is not a naphthyl group, a phenyl group substituted at the 4-position by a cyclohexyl, $C_{4-12}$ alkyl, $C_{6-12}$ alkoxy, $C_{4-8}$ alkylthio, ($C_{6-8}$ alkoxy)carbonyl, 4-methylphenylthio, 4-chlorophenylthio, benzyl, phenylethyl or dibutylamino group, a phenyl group substituted at the 3-position by a hexylthio group or a phenyl group substituted at the 3- and 4-position by a —$(CH_2)_4$— group;
  (ii) when p is 1, X is NH, m is 0, $R^1$ is $CH_3$ and n is 0 then $R^2$ is not a phenyl group substituted at the 4-position by a cyclohexyl or $C_{4-6}$ alkyl group; and
  (iii) when p is 1, X is NH, m is 0, $R^1$ is H, n is 2 and R is 5,5-dimethyl then $R^2$ is not a phenyl group substituted at the 4-position by a cyclohexyl group.

When the compounds in the compositions of the present invention contain an alkyl substituent group, this may be linear or branched and may contain up to 12, preferably up to 6, and especially up to 4, carbon atoms. An aryl group may be any aromatic hydrocarbon group, especially a phenyl group. An aralkyl group may be any alkyl group substituted by an aryl group, especially a benzyl group.

When any of the foregoing substituents are designated as being optionally substituted, the substituent groups which are optionally present may be any one or more of those customarily employed in the development of pesticidal compounds and/or the modification of such compounds to influence their structure/activity, persistence, penetration or other property. Specific examples of such substituents include, for example, halogen atoms, nitro, cyano, hydroxyl, cycloalkyl, alkyl, haloalkyl, alkoxy, haloalkoxy, amino, alkylamino, dialkylamino, formyl, alkoxycarbonyl, carboxyl, alkanoyl, alkylthio, alkylsulphinyl, alkylsulphonyl, carbamoyl and alkylamido groups. When any of the foregoing substituents represents or contains an alkyl substituent group, this may be linear or branched and may contain up to 12, preferably up to 6, and especially up to 4, carbon atoms.

It is preferred that, when p is 1, X is NH, m is 0, $R^1$ is H and n is 0 that $R^2$ is not a phenyl group substituted at the 3- and/or 4-position. More preferably, when p is 1, X is NH, m is 0, $R^1$ is H and n is 0 then $R^2$ is an unsubstituted phenyl group.

It is also preferred that when p is 1, X is NH, m is 0 and, either $R^1$ is $CH_3$ and n is 0, or $R^1$ is H, n is 2 and R is 5,5-dimethyl that $R^2$ is not a phenyl group substituted at the 4-position and is, most preferably, an unsubstituted phenyl group.

It is preferred that R represents a $C_1$-$C_6$ alkyl, phenyl or benzyl group each group being optionally substituted by one or more substituents selected from halogen atoms, hydroxyl, $C_1$-$C_4$ alkyl $C_1$-$C_4$ haloalkyl $C_1$-$C_4$ alkoxy, $C_1$-$C_4$ haloalkoxy, amino, $C_1$-$C_4$alkylamino, di-$C_1$-$C_4$ alkylamino, formyl, $C_1$-$C_4$ alkoxycarbonyl and carboxyl groups.

More preferably, R represents a phenyl or benzyl group, each group being optionally substituted by one or more substituents selected from halogen atoms and $C_1$-$C_4$ alkyl groups, or a $C_1$-$C_4$ alkyl, especially methyl, group.

It is preferred that $R^1$ represents a hydrogen atom or a $C_1$-$C_6$ alkyl or benzyl group, each group being optionally substituted by one or more substituents selected from halogen atoms, nitro, cyano, hydroxyl, $C_1$-$C_4$ alkyl, $C_1$-$C_4$ haloalkyl, $C_1$-$C_4$ alkoxy, $C_1$-$C_4$ haloalkoxy, amino, $C_1$-$C_4$ alkylamino, di-$C_1$-$C_4$ alkylamino, formyl, $C_1$-$C_4$ alkoxycarbonyl and carboxyl groups.

More preferably, represents a $C_1$-$C_4$ alkyl group or, especially, a hydrogen atom.

It is preferred that $R^2$ represents a phenyl group optionally substituted by one or more substituents selected from halogen atoms, hydroxyl, $C_1$-$C_4$ alkyl, $C_1$-$C_4$ haloalkyl, $C_1$-$C_4$ alkoxy, $C_1$-$C_4$ haloalkoxy, amino, $C_1$-$C_4$ alkylamino, di-$C_1$-$C_4$ alkylamino, formyl, $C_1$-$C_4$ alkoxycarbonyl and carboxyl groups.

More preferably, $R^2$ represents a phenyl group optionally substituted by a halogen, especially chlorine, atom or a $C_1$-$C_4$ alkyl, especially butyl, group.

Preferably, X represents a group —$NR^3$— or —$NR^3$—$NR^3$— where each $R^3$ independently represents a hydrogen atom or a $C_1$-$C_6$ alkyl group optionally substituted by one or more substituents selected from halogen atoms, hydroxyl, $C_1$-$C_4$ alkyl, $C_1$-$C_4$ haloalkyl, $C_1$-$C_4$ alkoxy, $C_1$-$C_4$ haloalkoxy, amino, $C_1$-$C_4$ alkylamino, di-$C_1$-$C_4$ alkylamino, formyl, $C_1$-$C_4$ alkoxycarbonyl and carboxyl groups. More preferably, each $R^3$ independently represents a hydrogen atom or a $C_1$-$C_4$ alkyl, especially a methyl, group.

It is preferred that when $R^1$ and $(X)_p$—A—$R^2$ together represent a group —$(CR^4R^5)_q$—N (A—$R^2$)— where $R^2$, q and A are as defined above, each of $R^4$ and $R^5$ is independently selected from a group consisting of hydrogen atoms and $C_1$-$C_6$ alkyl groups optionally substituted by one or more substituents selected from halogen atoms, nitro, cyano, hydroxyl, $C_1$-$C_4$ alkyl, $C_1$-$C_4$ haloalkyl, $C_1$-$C_4$ alkoxy, $C_1$-$C_4$ haloalkoxy, amino $C_1$-$C_4$ alkylamino di-$C_1$-$C_4$ alkylamino formyl preferably, each of $R^4$ and $R^5$ represents a hydrogen atom.

Preferably, A represents a group —$(CR^6R^7)_m$— where m is 0, 1, 2, 3 or 4 and each of $R^6$ and $R^7$ is independently selected from a group consisting of hydrogen atoms and $C_1$-$C_6$ alkyl groups optionally substituted by one or more substituents selected from halogen atoms, hydroxyl, $C_1$-$C_4$ alkyl, $C_1$-$C_4$ haloalkyl, $C_1$-$C_4$ alkoxy, $C_1$-$C_4$ haloalkoxy, amino, $C_1$-$C_4$ alkylamino, di-$C_1$-$C_4$ alkylamino, formyl, $C_1$-$C_4$ alkoxycarbonyl and carboxyl groups. More preferably, each of $R^6$ and $R^7$ is independently selected from a group consisting of hydrogen atoms and $C_1$-$C_4$ alkyl, especially methyl and ethyl, groups.

A particularly preferred sub-group of compounds of formula I is that in which n is 0, 1 or 2; R represents a methyl, phenyl, benzyl or butylbenzyl group; $R^1$ represents a hydrogen atom; $R^2$ represents a phenyl, chlorophenyl, methylphenyl, propylphenyl or butylphenyl group; p is 0 or 1; X represents a group —$NR^3$— or —$NR^3$—$NR^3$— where each $R^3$ represents a hydrogen atom; and A represents a group —$(CR^6R^7)_m$— where m is 0, 1, 2, 3 or 4 and each of $R^6$ and $R^7$ is independently selected from a group consisting of hydrogen atoms and methyl and ethyl groups.

Certain of the compounds of formula I are novel and the invention therefore also provides a compound of the general formula I as defined in claim 1 with the further provisos that (i) when p is 1, X is NH, m is 0, $R^1$ is H and n is 0 then $R^2$ is not a phenyl group substituted at the 4-position by a $C_3$ alkyl phenoxy, chlorophenoxy, methylphenoxy, dimethylphenoxy, ($C_{4-6}$ alkylthio) methyl, phenylthiomethyl, benzylthio, 2-chloroallylthio, benzyloxy, chlorobenzyloxy, methylphenyl-ethyl, propylphenyl-ethyl, $C_{2-4}$ alkoxyphenyl-ethyl, chlorophenyl-ethyl, furylethyl, stilbenyl or adamantyl group, or a phenyl group substituted at the 3-position by a chlorine atom and at the 4-position by a $C_3$alkylthio or phenoxy group; and when p is 1, X is NH, m is 0, $R^1$ is H, n is 1 and R is methyl then $R^2$ is not an octyl group.

It should also be appreciated that the compounds of formula I are capable of existing as different geometric, for example tautomeric, and optical isomers. The present invention thus includes both the individual isomers and mixtures of such isomers.

The present invention also provides a process for the preparation of a compound of formula I as defined in the ante-preceding paragraph or an acid-addition salt or metal salt complex thereof which comprises hydrogenating a compound of the general formula

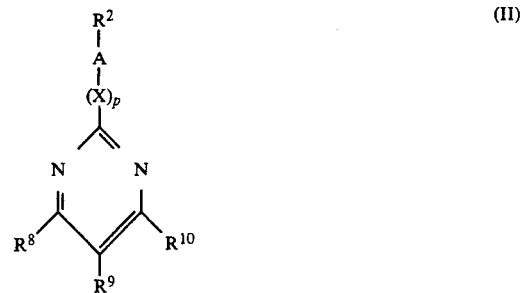

in which $R^8$ and $R^{10}$ each independently represent a group R or a hydrogen or halogen atom, $R^9$ represents a group R or a hydrogen atom and R, $R^2$, p, X and A are as defined above; if desired, reacting the compound of formula I so obtained with a compound of formula, $R^{1'}L$, where $R^{1'}$ represents an optionally substituted alkyl or aralkyl group and L represents a leaving group, in the presence of a base; and, if desired, reacting the compound of formula I so obtained with an acid or metal salt to form an acid-addition salt or metal salt complex thereof.

The process of the invention is conveniently carried out in the presence of a solvent. Suitable solvents include polar solvents such as water, alcohols, particularly ethanol, and mixtures thereof, ethyl acetate and ethers, such as tetrahydrofuran.

The hydrogenation step may take place in the presence of an acid catalyst, such as hydrochloric acid.

Suitable leaving groups include halogen, especially chlorine, bromine and iodine, atoms and mesylate and tosylate groups.

Suitable bases include alkali metal carbonates, especially potassium carbonate, alkali metal hydroxides, especially sodium hydroxide, and organic bases such as tertiary amines, for example, triethylamine.

The reaction is suitably carried out at a temperature from 0° C. to 100° C., the preferred reaction temperature being from 15° C. to 70° C.

Conveniently, a compound of formula II in which one or both of $R^8$ and $R^{10}$ represents a halogen atom is prepared by reacting a compound of the general formula

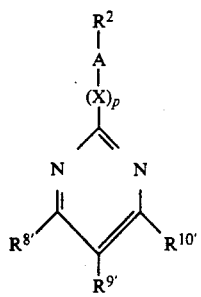

(III)

in which one or both of $R^{8'}$ and $R^{10'}$ represents a hydroxyl group and the other represents a group R or a hydrogen atom, $R^{9'}$ represents a group R or a hydrogen atom and R, $R^2$, p, X and A are as defined above, with a suitable halogenating agent, such as phosphorus oxychloride.

A compound of formula III in which p is 0 may conveniently be prepared by reacting a compound of the general formula

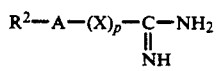

(IV)

or an acid-addition salt thereof, in which p is 0 and $R^2$, X and A are as defined above, with a compound of the general formula

(V)

in which $R^{11}$ represents a group R or —$OR^{13}$, $R^{12}$ represents a group R or a hydrogen atom, $R^{13}$ represents an alkyl, preferably a $C_{1-6}$ alkyl group and R is as defined above, in the presence of a strong base such as sodium ethoxide.

Compounds of formula IV may be prepared by the method of D. J. Brown, B. J. Cronin, S. -B. Lan and G. Nardo, Aust. J. Chem, (1985), 38, 825 and certain compounds of formula V may be prepared by the method of C. R. Holmquist and E. J. Roskamp, J. Org. Chem., (1989), 54, 3258. Other compounds of formula V are known compounds or can be prepared by processes analogous to known processes.

Alternatively, a compound of formula III in which $R^{8'}$ and $R^{9'}$, $R^{9'}$ and $R^{10'}$ or one of $R^{8'}$, $R^{9'}$ and $R^{10'}$ independently represent a group R as defined above and p is 1 or 2 may conveniently be prepared by reacting a compound of the general formula

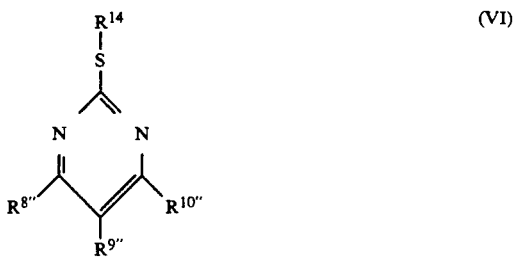

(VI)

in which $R^{8''}$ and $R^{9''}$, $R^{9''}$ and $R^{10''}$ or one of $R^{8''}$, $R^{9''}$ and $R^{10''}$ independently represent a group R as defined above and the others represent a hydroxyl group or a hydrogen atom and $R^{14}$ represents an alkyl, preferably $C_1$-$C_6$ alkyl and especially methyl, group, with a compound of the general formula

$$R^2—A—(X)_p—H$$ (VII)

in which p is 1 or 2 and $R^2$ X and A are as defined above.

A compound of formula VI may conveniently be prepared by reacting a compound of the general formula

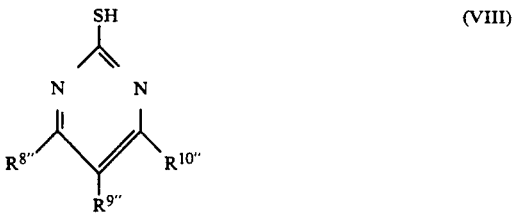

(VIII)

in which $R^{8''}$ and $R^{9''}$, $R^{9''}$ and $R^{10''}$ or one of $R^{8''}$, $R^{9''}$ and $R^{10''}$ independently represent a group R as defined above and the others represent a hydroxyl group or a hydrogen atom, with a compound of the general formula

$$R^{14}—L^1$$ (IX)

in which $R^{14}$ is as defined above and $L^1$ represents a leaving group, in the presence of a base, such as triethylamine. Preferably the leaving group is a halogen, especially iodine, atom.

A compound of formula VIII may conveniently be prepared by reacting a compound of formula V as defined above with thiourea in the presence of a strong base, such as sodium in ethanol.

A compound of formula VII in which p is 1, X represents a group —$NR^3$— where $R^3$ represents a hydrogen atom and A represents a group —$(CR^6R^7)_{m'}$- where m' is 2, 3 or 4, may conveniently be prepared by reducing a compound of the general formula $$R^2-(CR^6R^7)_t-CR^{15}=CR^{16} \quad (X)$$
$$\qquad\qquad\qquad\quad |$$
$$\qquad\qquad\qquad\quad NO_2$$

in which $R^2$, $R^6$ and $R^7$ are as defined above, t is 0, 1 or 2 and $R^{15}$ and $R^{16}$ are each independently selected from a group consisting of hydrogen atoms and optionally substituted alkyl groups, with a suitable reducing agent such as lithium aluminium hydride. Other compounds of formula VII are known compounds or can be prepared by processes analogous to known processes.

Compounds of formula X in which t is 0 may be prepared by the method of M. J. Ferris, EP-A1-0 040 000. Compounds of formula X in which t is 1 or 2 may be prepared by the method of J. Melton and J. E. McMurray, J. Org. Chem., (1975), 40, 2138.

Alternatively, a compound of formula II in which $R^8$ and $R^{10}$ or $R^8$, $R^9$ and $R^{10}$ each independently represent a group R as defined above or $R^8$, $R^9$ and $R^{10}$ each represent hydrogen and p is 1 or 2 may be conveniently prepared by reacting a compound of the general formula (XI) — structure with $L^2$, N, N ring with $R^8$, $R^9$, $R^{10}$ in which $R^8$, $R^9$ and $R^{10}$ are as defined above and $L^2$ represents a leaving group, with a compound of formula VII as defined above. Preferably, the leaving group is a halogen atom or an alkylsulphonyl group $-SO_2R^{14}$ where $R^{14}$ is as defined above.

A compound of formula XI in which $L^2$ represents a halogen atom may be prepared by the method of S. Angerstein, Berichte, (1901), 34, 3956 or by a process analogous thereto.

A compound of formula XI in which $L^2$ represents an alkylsulphonyl group $-SO_2R^{14}$ may conveniently be prepared by oxidising a compound of the general formula (XII) — structure with $R^{14}$-S, N, N ring with $R^8$, $R^9$, $R^{10}$ in which $R^8$, $R^9$, $R^{10}$ and $R^{14}$ are as defined above with a suitable oxidising agent, such as hydrogen peroxide or a peroxyacid, for example, m-chloroperoxybenzoic acid.

A compound of formula XII may conveniently be prepared by reacting a compound of the general formula (XIII) — structure with SH, N, N ring with $R^8$, $R^9$, $R^{10}$ in which $R^8$, $R^9$ and $R^{10}$ are as defined above, with a compound of formula IX as defined above, in the presence of a base such as triethylamine, potassium carbonate or an alkali metal hydroxide.

Compounds of formula IX and XIII are known compounds or can be prepared by processes analogous to known processes.

The compounds of formula I may also be prepared by reacting a compound of formula (XIV) — structure with $SCH_3$, $R^1N$, N, $(R)_n$ in which n, R and $R^1$ are as defined above, with a compound of formula VII as defined above in the presence of a base. The base may be an inorganic base, such as potassium carbonate, or, more preferably, an excess of the compound of formula VII. Conveniently, the reaction takes place at a temperature of 100° C.-160° C. An analogous method is described in more detail in EP 0389765 A1.

A compound of formula XIV may be prepared by reacting a compound of formula (XV) — structure with S, $R^1N$, NH, $(R)_n$ in which n, R and $R^1$ are as defined above, with a suitable methylating agent, such as methyl sulphate, methyl bromide or, most preferably, methyl iodide. Conveniently, the reaction may be carried out in an organic solvent in the presence of a base, such as potassium carbonate or triethylamine, at a temperature from 0° C.-30° C. A more detailed description of an analogous method is given in EP 0389765 A1.

A compound of formula XV may be prepared by reacting a compound of formula (XVI) — structure with O, $R^1N$, NH, $(R)_n$ in which n, R and R¹ are as defined above, with a suitable thiating agent, such as phosphorous pentasulphide according to the method of H. Beringer and H. Meier, Ann., (1957), 607, 67. Conveniently, the reaction may be carried out in a high boiling solvent, such as xylene or 1,4-dioxane, at a temperature of 90° C.–150° C.

Compounds of formula XVI may be prepared according to the method of R. O. Hutchins and B. E. Maryanoff, J. Org. Chem., (1972), 37, 1829.

The compounds of general formula I have been found to have fungicidal activity. Accordingly, the invention provides a fungicidal composition which comprises a carrier and, as active ingredient, a compound of formula I or an acid-addition salt or metal salt complex thereof as defined above. A method of making such a composition is also provided which comprises bringing a compound of formula I as defined above, or an acid-addition salt or metal salt complex thereof, into association with at least one carrier. Such a composition may contain a single compound or a mixture of several compounds of the present invention. It is also envisaged that different isomers or mixtures of isomers may have different levels or spectra of activity and thus compositions may comprise individual isomers or mixtures of isomers.

A composition according to the invention preferably contains from 0.5 to 95% by weight of active ingredient.

A carrier in a composition according to the invention is any material with which the active ingredient is formulated to facilitate application to the locus to be treated, which may for example be a plant, seed or soil, or to facilitate storage, transport or handling. A carrier may be a solid or a liquid, including a material which is normally gaseous but which has been compressed to form a liquid, and any of the carriers normally used in formulating fungicidal compositions may be used.

Suitable solid carriers include natural and synthetic clays and silicates, for example natural silicas such as diatomaceous earths; magnesium silicates, for example talcs; magnesium aluminium silicates, for example attapulgites and vermiculites; aluminium silicates, for example kaolinites, montmorillonites and micas; calcium carbonate; calcium sulphate; ammonium sulphate; synthetic hydrated silicon oxides and synthetic calcium or aluminium silicates; elements, for example carbon and sulphur; natural and synthetic resins, for example coumarone resins, polyvinyl chloride, and styrene polymers and copolymers; solid polychlorophenols; bitumen; waxes, for example beeswax, paraffin wax, and chlorinated mineral waxes; and solid fertilisers, for example superphosphates.

Suitable liquid carriers include water; alcohols, for example isopropanol and glycols; ketones, for example acetone, methyl ethyl ketone, methyl isobutyl ketone and cyclohexanone; ethers; aromatic or araliphatic hydrocarbons, for example benzene, toluene and xylene; petroleum fractions, for example kerosine and light mineral oils; chlorinated hydrocarbons, for example carbon tetrachloride, perchloroethylene and trichloroethane. Mixtures of different liquids are often suitable.

Fungicidal compositions are often formulated and transported in a concentrated form which is subsequently diluted by the user before application. The presence of small amounts of a carrier which is a surface-active agent facilitates this process of dilution. Thus preferably at least one carrier in a composition according to the invention is a surface-active agent. For example the composition may contain at least two carriers, at least one of which is a surface-active agent.

A surface-active agent may be an emulsifying agent, a dispersing agent or a wetting agent; it may be nonionic or ionic. Examples of suitable surface-active agents include the sodium or calcium salts of polyacrylic acids and lignin sulphonic acids; the condensation products of fatty acids or aliphatic amines or amides containing at least 12 carbon atoms in the molecule with ethylene oxide and/or propylene oxide; fatty acid esters of glycerol, sorbitol, sucrose or pentaerythritol; condensates of these with ethylene oxide and/or propylene oxide; condensation products of fatty alcohol or alkyl phenols, for example p-octylphenol or p-octylcresol, with ethylene oxide and/or propylene oxide; sulphates or sulphonates of these condensation products; alkali or alkaline earth metal salts, preferably sodium salts, of sulphuric or sulphonic acid esters containing at least 10 carbon atoms in the molecule, for example sodium lauryl sulphate, sodium secondary alkyl sulphates, sodium salts of sulphonated castor oil, and sodium alkylaryl sulphonates such as dodecylbenzene sulphonate; and polymers of ethylene oxide and copolymers of ethylene oxide and propylene oxide.

The compositions of the invention may for example be formulated as wettable powders, dusts, granules, solutions, emulsifiable concentrates, emulsions, suspension concentrates and aerosols. Wettable powders usually contain 25, 50 or 75% w of active ingredient and usually contain in addition to solid inert carrier, 3–10% w of a dispersing agent and, where necessary, 0–10% w of stabiliser(s) and/or other additives such as penetrants or stickers. Dusts are usually formulated as a dust concentrate having a similar composition to that of a wettable powder but without a dispersant, and may be diluted in the field with further solid carrier to give a composition usually containing ½–10% w of active ingredient. Granules are usually prepared to have a size between 10 and 100 BS mesh (1.676–0.152 mm), and may be manufactured by agglomeration or impregnation techniques. Generally, granules will contain ½–75% w active ingredient and 0–10% w of additives such as stabilisers, surfactants, slow release modifiers and binding agents. The so-called "dry flowable powders" consist of relatively small granules having a relatively high concentration of active ingredient. Emulsifiable concentrates usually contain, in addition to a solvent and, when necessary, co-solvent, 1–50% w/v active ingredient, 2–20% w/v emulsifiers and 0–20% w/v of other additives such as stabilisers, penetrants and corrosion inhibitors. Suspension concentrates are usually compounded so as to obtain a stable, non-sedimenting flowable product and usually contain 10–75% w active ingredient, 0.5–15% w of dispersing agents, 0.1–10% w of suspending agents such as protective colloids and thixotropic agents, 0–10% w of other additives such as defoamers, corrosion inhibitors, stabilisers, penetrants and stickers, and water or an organic liquid in which the active ingredient is substantially insoluble; certain organic solids or inorganic salts may be present dissolved in the formulation to assist in preventing sedimentation or as antifreeze agents for water.

Aqueous dispersions and emulsions, for example compositions obtained by diluting a wettable powder or a concentrate according to the invention with water, also lie within the scope of the invention. The said emulsions may be of the water-in-oil or of the oil-in-water type, and may have a thick 'mayonnaise' like consistency.

The composition of the invention may also contain other ingredients, for example other compounds possessing herbicidal, insecticidal or fungicidal properties.

Of particular interest in enhancing the duration of the protective activity of the compounds of this invention is the use of a carrier which will provide a slow release of the fungicidal compounds into the environment of the plant which is to be protected. Such slow-release formulations could, for example, be inserted in the soil adjacent to the roots of a vine plant, or could include an adhesive component enabling them to be applied directly to the stem of a vine plant.

The present invention still further provides the use as a fungicide of a compound of the general formula I as defined above or an acid-addition salt or metal salt complex thereof or a composition as defined above, and a method for combating fungus at a locus, which comprises treating the locus, which may be for example plants subject to or subjected to fungal attack, seeds of such plants or the medium in which such plants are growing or are to be grown, with such a compound or composition.

The present invention is of wide applicability in the protection of crop plants against fungal attack. Typical crops which may be protected include vines and grain crops such as wheat and barley. The duration of protection is normally dependent on the individual compound selected, and also a variety of external factors, such as climate, whose impact is normally mitigated by the use of a suitable formulation.

The invention is further illustrated by the following examples.

EXAMPLE 1

Preparation of
2-(1-Methyl-2-[4t-Butylphenyl]Ethyl)Amino-4,6-Cis Dimethyl-3,4,5,6-Tetrahydropyrimidine Hydrochloride
(n=2; R=4-Methyl, 6-Methyl; $R^1$=Hydrogen;
$R^2$=4t-Butylphenyl; p=1; X=—NH—;
A=CH(CH$_3$)CH$_2$—)

(i) Preparation of 2-Amino-1-(4-t-Butylphenyl)Propane

A solution of 1-(4-t-butylphenyl)-2-nitroprop-1-ene (2.19 g, 10 mmol) in tetrahydrofuran (50ml) was added, over a period of 20 minutes, to a solution of lithium aluminium hydride (1.14 g, 30 mmol) in tetrahydrofuran (50 ml). The reaction mixture was then heated under reflux for 20 hours, cooled and worked up with saturated aqueous sodium sulphate solution. The mixture was filtered through Hyflo (Trade mark; diatomaceous earth) and the pad washed well with ethyl acetate. Evaporation in vacuo followed by flash column chromatography upon silica gel using 85:10:5 - ethyl acetate: methanol: triethylamine as eluant afforded 1.42 g 2-amino-1-(4-t-butylphenyl)propane as a clear, colourless oil. Low resolution mass spectroscopy revealed the mass/charge ratio of the parent molecule ion, M+, to be 191 thereby confirming the molecular weight of the product to be 191.

Analysis Calc: C: 81.6; H: 11.1; N: 7.3% Found: C: 81.1; H: 11.3; N: 7.2%

(ii) Preparation of
2-Methylsulphonyl-4,6-Dimethylpyrimidine

A suspension of potassium carbonate (27.6 g, 0.2 mol) in a solution of 4,6-dimethyl-2-mercaptopyrimidine (14 g, 0.1 mol) and methyl iodide (18.7 ml, 0.3 mol) in acetone (200 ml) was heated under reflux for 3 hours. The reaction mixture was allowed to cool before being filtered and then evaporated in vacuo. Distillation of the mixture at a pressure of 0.01 mmHg afforded 12.7 g 2-methylthio-4,6-dimethylpyrimidine as a white solid. A portion of this solid (4.42 g, 28.7 mmol) was dissolved in dichloromethane (200ml) and m-chloroperoxybenzoic acid (50%, 22.8 g, 66.0 mmol) was added in portions. The resulting mixture was stirred for a period of 5 days at the end of which it was first filtered and then evaporated in vacuo. Purification by flash column chromatography upon silica gel using diethyl ether as eluant afforded 3.35 g 2-methylsulphonyl-4,6-dimethylpyrimidine as a white solid, m.pt., 81° C.

(iii) Preparation of
2-(1-Methyl-2-[4-t-Butylphenyl]Ethyl)Amino-4,6-Dimethylpyrimidine A mixture of the 2-amino-1-(4-t-butylphenyl)propane (2.57 g, 13.4 mmol) obtained in (i) and the 2-methylsulphonyl-4,6-dimethylpyrimidine (2.5 g, 13.4 mmol) obtained in (ii) was heated with stirring at 135° C. for 5 hours. After the reaction mixture had cooled, it was dissolved in ethyl acetate (50 ml) and then washed with saturated aqueous sodium bicarbonate solution (10 ml). The mixture was then dried over sodium sulphate followed by evaporation in vacuo. Purification by flash column chromatography, upon silica gel using 3:1 diethyl ether:hexanes as eluant afforded 1.61 g 2-(1-methyl-2-[4-t-butylphenyl]ethyl)amino-4,6-dimethylpyrimidine as a faintly yellow oil. M+ found: 297.

Analysis Calc. C: 76.7; H: 9.1; N: 14.1% Found C: 77.4; H: 9.4; N: 14.2%

(iv) Preparation of
2-(1-Methyl-2-[4-t-Butylphenyl]ethyl)amino-4,6-dimethyl-3,4,5,6-tetrahydropyrimidine A solution of the 2-(1-methyl-2-[4-t-butylphenyl]ethyl)amino-4,6-dimethylpyrimidine (1.24 g, 4.18 mmol) obtained in (iii) in 0.5M ethanolic hydrogen chloride (100 ml) was hydrogenated at about 3 atmospheres in the presence of 10% palladium on charcoal catalyst (320 mg) until hydrogen uptake had ceased. The solution was then filtered to remove the catalyst and the filtrate evaporated. Addition of dichloromethane (20 ml) and evaporation afforded 1.08 g 2-(1-methyl-2-[4-t-butylphenyl]ethyl)amino-4,6-dimethyl-3,4,5,6-tetrahydropyrimidine hydrochloride (in hemi-hydrate form) as an off-white foam, m.pt., 40°–45° C. M+ (—HCl) found: 301.

Analysis (for hemi-hydrate) Calc. C: 65.8; H: 9.2; N: 11.8% Found C: 65.8; H: 9.6; N: 12.1%

EXAMPLE 2

Preparation of
2,4-Di(Phenylmethyl)-3,4,5,6-Tetrahydropyrimidine hydrochloride (n=1; R=4-Benzyl; $R^1$=Hydrogen; $R^2$=Phenyl; p=0; A=—CH$_2$—)

(i) Preparation of
2,4-Di(Phenylmethyl)-6-Hydroxypyrimidine

To a solution of sodium (1.84 g, 80 mmol) in ethanol (200 ml) was added phenylacetamidine hydrochloride (16.2 g, 95.0 mmol) and ethyl 4-phenylacetoacetate (15 g, 72.9 mmol). The mixture was heated under reflux with stirring for 5 days followed by cooling and evaporation in vacuo. Water (150 ml) was added to the residue causing a solid to precipitate which was filtered off and washed thoroughly with water and diethyl ether. Recrystallisation of the solid from a chloroform/hexane mixture afforded 6.9 g 2,4-di(phenylmethyl)-6-hydroxypyrimidine as a white solid. m.pt., 158°-160° C., M+ found: 276.

Analysis Calc. C: 78.2; H: 5.8; N: 10.1% Found C: 77.8; H: 5.9; N: 10.2%

(ii) Preparation of 2,4-Di(Phenylmethyl)-6-Chloropyrimidine

A mixture of phosphorus oxychloride (125 ml) and the 2,4-di(phenylmethyl)-6-hydroxypyrimidine (6.37 g, 22.9 mmol) obtained in (i) was heated under reflux for 5 hours. The excess phosphorus oxychloride was distilled off to leave a residue. Crushed ice was added to the cooled residue with caution until all reaction had ceased. Water (100 ml) was then added and the mixture extracted with chloroform (3×50 ml). The combined organic phases were washed with saturated aqueous sodium bicarbonate solution (10 ml) and dried over sodium sulphate. Evaporation in vacuo followed by flash column chromatography upon silica gel using chloroform as eluant afforded 2.56 g 2,4-di(phenylmethyl)-6-chloropyrimidine as a light yellow oil. M+ found: 294/296.

Analysis Calc. C: 73.3; H: 5.1; N: 9.5% Found C: 72.8; H: 5.0; N: 9.4%

(iii) Preparation of 2,4-Di(Phenylmethyl)-3,4,5,6-Tetrahydropyrimidine Hydrochloride A solution of the 2,4-di(phenylmethyl)-6-chloropyrimidine (2.3 g, 7.81 mmol) obtained in (ii) in ethanol (50 ml) and water (5 ml) was hydrogenated at about 3 atmospheres in the presence of 10% palladium on charcoal catalyst (380 mg) until hydrogen uptake had ceased. After filtration through Hyflo (Trade mark; diatomaceous earth) to remove the catalyst, the solution was evaporated in vacuo. Addition of ethanol (50 ml) and evaporation followed by addition of toluene (50 ml) and evaporation afforded a white foam which was dried at 45° C., at a pressure of 20mmHg for 48 hours, to give 2.3 g 2,4-di(phenylmethyl)-3,4,5,6-tetrahydropyrimidine hydrochloride, m.pt., 50°-57° C. (deliquesces). M+ (-HCl) found: 264.

Analysis Calc. C: 71.9; H: 7.0; N: 9.3% Found C: 72.9; H: 7.0; N: 8.6%

EXAMPLE 3

Preparation of 2-Phenylamino-4-Phenylmethyl-3,4,5,6-Tetrahydropyrimidine hydrochloride (n=1; R=4-benzyl; $R^1$=hydrogen $R^2$=phenyl; p=1; X=—NH—; m=0)

(i) Preparation of 4-Hydroxy-6-Phenylmethyl-2-Mercaptopyrimidine

Sodium (11.5 g, 0.5 mol) was dissolved in ethanol (700 ml) and ethyl 4-phenylacetoacetate added with mechanical stirring. Further ethanol (350 ml) and thiourea (22.8 g, 0.3 mol) were added and the reaction mixture heated under reflux for 24 hours. The reaction mixture was then cooled, poured into water (2 liters) and acidified with concentrated hydrochloric acid to approximately pH5. The resulting precipitate was filtered off, washed with water (3×500 ml) and diethyl ether (2×300 ml) and dried under vacuum to afford 41.5 g 4-hydroxy-6-phenylmethyl-2-mercaptopyrimidine as a beige solid, m.pt., 215°-220° C. with decomposition. M+ found: 218.

Analysis Calc. C: 60.5; H: 4.6; N: 12.8% Found C: 61.1; H: 5.2; N: 11.9%

(ii) Preparation of 4-Hydroxy-6-Phenylmethyl-2-Methylthiopyrimidine

Triethylamine (28.1 ml, 0.202 mol) was added dropwise, over 30 minutes, to a stirred solution of the 4-hydroxy-6-phenylmethyl-2-mercaptopyrimidine (40 g, 0.183 mol) obtained in (i) and iodomethane (13.7 ml, 0.22 mol) in dimethylsulphoxide (250 ml). After 4 hours, the reaction mixture was poured into water (1.5 liters) and 2N hydrochloric acid (20 ml) added. The precipitate was filtered off, washed with water (2×400 ml) and diethyl ether (2×300 ml) and, finally, dried under vacuum to afford 34.8 g 4-hydroxy-6-phenylmethyl-2-methylthio-pyrimidine as a beige solid, m.pt., 175°-176° C. M+ found: 232.

Analysis Calc. C: 62.0; H: 5.2; N: 12.1% Found C: 61.2; H: 5.2; N: 12.0%

(iii) Preparation of 4-Hydroxy-6-Phenylmethyl-2-Phenylaminopyrimidine

A mixture of the 4-hydroxy-6-phenylmethyl-2-methylthiopyrimidine (10 g, 43.1mmol) obtained in (ii) and aniline (9.8 ml, 108 mmol) were heated for 5 hours at 140° C. The reaction mixture was then cooled and ethanol (75 ml) added before refluxing for 1 hour. After cooling, the solid was filtered off, washed with ethanol (3×50 ml) and, finally, dried under vacuum to afford 10.7 g 4-hydroxy-6-phenylmethyl-2-phenylaminopyrimidine as a beige solid, m.pt., 195°-197° C. M+ found: 277.

Analysis Calc. C: 73.6; H: 5.5; N: 15.2% Found C: 73.1; H: 5.5; N: 15.1%

(iv) Preparation of 4-Chloro-6-Phenylmethyl-2-Phenylaminopyrimidine

A mixture of the 4-hydroxy-6-phenylmethyl-2-phenylaminopyrimidine (3.0 g, 10.5 mmol) obtained in (iii), phosphorus oxychloride (50 ml, 54.2 mmol) and N,N-dimethylaniline (2.3 ml, 18.4 mmol) were refluxed together with stirring for a period of 3 hours. The excess phosphorus oxychloride was distilled off and then crushed ice was added with caution to the cooled residue. Water (30 ml) was then added and the reaction mixture extracted with chloroform (3×50 ml). The combined organic extracts were washed with brine (20 ml) and subsequently dried over sodium sulphate. Evaporation in vacuo followed by flash column chromatography upon silica gel using 3:1 petroleum ether: diethyl ether as eluant afforded 0.77 g 4-chloro-6-phenylmethyl-2-phenylaminopyrimidine as a light green oil. M+ found: 295/297.

Analysis Calc. C: 69.0; H: 4.8; N: 14.2% Found C: 68.0; H: 4.7; N: 13.5%

(v) Preparation of 2-Phenylamino-4-Phenylmethyl-3,4,5,6-Tetrahydropyrimidine Hydrochloride A mixture of the 4-chloro-6-phenylmethyl-2-phenylaminopyrimidine (0.57 g, 1.93 mmol) obtained in (iv) and 10% palladium on charcoal (100 mg) in water (1 ml) and ethanol (50 ml) was Paar hydrogenated at 3 atmospheres until hydrogen uptake had ceased. The reaction mixture was then filtered through Hyflo (Trade mark; diatomaceous earth) and subsequently evaporated in vacuo. Addition of dichloromethane (50 ml) to the residue followed by evaporation afforded 0.57 g 2-phenylamino-4-phenylmethyl-3,4,5,6-tetrahydropyrimidine hydrochloride as a white foam. M+ (-HCl) found: 265

Analysis (for mono-hydrate) Calc. C: 63.8; H: 6.9; N: 13.1% Found C: 64.0; H: 7.3; N: 12.7%

EXAMPLES 4 TO 31

By processes similar to those described in Examples 1 to 3 above, further compounds according to the invention were prepared as detailed in Table I below. In this table, the compounds are identified by reference to formula I. Low resolution mass spectroscopy and C, H, N analysis data for the compounds of Examples 4 to 31 are given in Table IA below.

TABLE I

| Example No. | n | R | $R^1$ | $R^2$ | p | X | A |
|---|---|---|---|---|---|---|---|
| 4 (saccharin salt) | 2 | 4-$CH_3$, 6-$CH_3$ | —H | 4-t-butylphenyl | 1 | —NH— | —CH($CH_3$)$CH_2$— |
| 5 (HCl salt) | 2 | 4-$CH_3$, 6-$CH_3$ | —H | 4-t-butylphenyl | 1 | —NH— | —CH($CH_3$)$CH_2$— |
| 6 (HCl salt) | 1 | 4-benzyl | —H | phenyl | 0 | — | single bond (i.e., m = 0) |
| 7 (HCl salt) | 1 | 4-benzyl | —H | phenyl | 0 | — | —$CH_2CH_2$— |
| 8 (HCl salt) | 1 | 4-benzyl | —H | 4-chlorophenyl | 0 | — | —$CH_2$— |
| 9 (HCl salt) | 1 | 5-benzyl | —H | phenyl | 1 | —NH— | —$CH_2$— |
| 10 (HCl salt) | 1 | 5-benzyl | —H | phenyl | 1 | —NH— | single bond (i.e., m = 0) |
| 11 (HCl salt) | 1 | 5-(4-t-butylbenzyl) | —H | phenyl | 1 | —NH— | single bond (i.e., m = 0) |
| 12 (HCl salt) | 1 | 5-(4-t-butylbenzyl) | —H | phenyl | 1 | —NH— | —$CH_2$— |
| 13 (HCl salt) | 2 | 4-$CH_3$, 6-$CH_3$ | —H | 2-methylphenyl | 1 | —NH—NH— | —CH($CH_3$)— |
| 14 | 1 | 5-(4-t-butylbenzyl) | —H | phenyl | 1 | —NH— | single bond (i.e., m = 0) |
| 15 | 1 | 5-(4-t-butylbenzyl) | —H | phenyl | 1 | —NH— | —$CH_2$— |
| 16 (HCl salt) | 2 | 4-$CH_3$, 6-$CH_3$ | —H | 4-t-butylphenyl | 1 | —NH—NH— | —CH($CH_3$)— |
| 17 (HCl salt) | 1 | 4-(4-t-butylbenzyl) | —H | phenyl | 1 | —NH— | single bond (i.e., m = 0) |
| 18 | 1 | 4-(4-t-butylbenzyl) | —H | phenyl | 1 | —NH— | single bond (i.e., m = 0) |
| 19 | 1 | 4-benzyl | —H | 4-chlorophenyl | 0 | — | —$CH_2$— |
| 20 | 1 | 4-benzyl | —H | phenyl | 0 | — | —$CH_2CH_2$— |
| 21 | 1 | 4-benzyl | —H | phenyl | 0 | — | single bond (i.e., m = 0) |
| 22 | 1 | 4-benzyl | —H | phenyl | 0 | — | —$CH_2$— |
| 23 (HCl salt) | 1 | 4-(4-t-butylbenzyl) | —H | phenyl | 1 | —NH— | —$CH_2$— |
| 24 (HCl salt) | 1 | 5-phenyl | —H | phenyl | 1 | —NH— | —$CH_2$— |
| 25 | 1 | 5-phenyl | —H | phenyl | 1 | —NH— | —$CH_2$— |
| 26 (HCl salt) | 1 | 5-phenyl | —H | phenyl | 1 | —NH— | single bond (i.e., m = 0) |
| 27 | 1 | 5-phenyl | —H | phenyl | 1 | —NH— | single bond (i.e., m = 0) |
| 28 (HCl salt) | 0 | — | —H | 4-t-butylphenyl | 1 | —NH— | —CH($CH_3$)$CH_2$— |
| 29 (HCl salt) | 2 | 4-$CH_3$, 6-$CH_3$ | —H | 4-t-butylphenyl | 1 | —NH— | —CH($C_2H_5$)$CH_2$— |
| 30 (HCl salt) | 2 | 4-$CH_3$, 6-$CH_3$ | —H | 4-isopropylphenyl | 1 | —NH— | —CH($CH_3$)$CH_2$— |
| 31 (HCl salt) | 2 | 4-$CH_3$, 6-$CH_3$ | —H | 4-t-butylphenyl | 1 | —NH— | —$CH_2$— |
| 32 (HCl salt) | 2 | 4-$CH_3$, 6-$CH_3$ | —H | phenyl | 1 | —NH— | —CH($CH_3$)$CH_2$— |
| 33 (HCl salt) | 2 | 4-$CH_3$, 6-$CH_3$ | —H | 4-t-butylphenyl | 1 | —N($CH_3$)—NH— | —CH($CH_3$)— |
| 34 (HI salt) | 0 | — | —H | phenyl | 1 | —NH— | —$CH_2CH_2$— |
| 35 (HI salt) | 0 | — | —H | 4-t-butylphenyl | 1 | —NH— | —CH($CH_3$)$CH_2$— |
| 36 (HI salt) | 0 | — | —H | 4-chlorophenyl | 1 | —NH— | —CH($CH_3$)$CH_2$— |
| 37 (HCl salt) | 2 | 4-$CH_3$, 6-$CH_3$ | —H | 4-methylphenyl | 1 | —NH— | —$CH_2$— |
| 38 (HCl salt) | 2 | 4-$CH_3$, 6-$CH_3$ | —H | 4-t-butylphenyl | 1 | —N($CH_3$)— | —CH($CH_3$)$CH_2$— |
| 39 (HCl salt) | 2 | 4-$CH_3$, 6-$CH_3$ | —H | 4-t-butylphenyl | 1 | —NH— | —CH($CH_3$)$CH_2CH_2$— |
| 40 (HCl salt) | 2 | 4-$CH_3$, 6-$CH_3$ | —H | 4-methylphenyl | 1 | —NH— | —CH($CH_3$)$CH_2$— |
| 41 (HI salt) | 2 | 4-$CH_3$, 6-$CH_3$ | —H | 4-chlorophenyl | 1 | —NH— | —$CH_2$— |
| 42 (HCl salt) | 2 | 4-$CH_3$, 6-$CH_3$ | —H | 4-t-butylphenyl | 1 | —NH— | —CH($CH_3$)$CH_2CH_2CH_2$— |

TABLE IA

| Example No. | m. pt °C. | M+ Found | Analysis % C Calc. | C Found | H Calc. | H Found | N Calc. | N Found |
|---|---|---|---|---|---|---|---|---|
| 4*** | 40–44 | 301 (—saccharin) | 60.0 | 60.3 | 7.7 | 7.2 | 10.9 | 10.9 |
| 5* | | 301 | 64.2 | 64.4 | 10.5 | 10.1 | 11.8 | 11.1 |
| 6 | 50–57 | 250 (—HCl) | 71.2 | 70.5 | 6.7 | 6.5 | 9.8 | 10.3 |
| 7 | 140–143 | 278 (—HCl) | 72.5 | 71.8 | 7.4 | 7.4 | 8.9 | 9.1 |
| 8 | 50–52 | — | 64.5 | 63.4 | 6.0 | 6.2 | 8.4 | 8.2 |
| 9 | 204 | — | 68.5 | 66.3 | 7.0 | 6.9 | 13.3 | 13.2 |
| 10 | | 265 | 67.7 | 65.5 | 6.7 | 6.6 | 13.9 | 13.4 |
| 11 | | 321 (—HCl) | 70.5 | 70.4 | 7.9 | 7.8 | 11.7 | 11.8 |
| 12 | | — | 71.0 | 69.8 | 8.1 | 7.7 | 11.3 | 11.3 |

TABLE IA-continued

| Example No. | m. pt °C. | M+ Found | Analysis % | | | | | |
|---|---|---|---|---|---|---|---|---|
| | | | C Calc. | C Found | H Calc. | H Found | N Calc. | N Found |
| 13 | 170 | 260 (—HCl) | 60.7 | 61.0 | 8.5 | 8.3 | 18.9 | 19.0 |
| 14*** | 65 | 321 | 70.6 | 70.5 | 8.7 | 7.6 | 11.8 | 11.6 |
| 15**** | 195 | 335 | 67.8 | 67.4 | 9.1 | 7.6 | 10.8 | 10.3 |
| 16 | | 302 (—HCl) | 63.8 | 63.2 | 9.2 | 9.1 | 16.5 | 16.4 |
| 17 | | 321 (—HCl) | 70.5 | 68.3 | 7.9 | 7.8 | 11.7 | 11.4 |
| 18* | | 321 | 76.3 | 76.0 | 8.5 | 8.4 | 12.7 | 12.2 |
| 19 | | | | | | | | |
| 20 | | 278 | | | | | | |
| 21 | | 250 | | | | | | |
| 22 | | 264 | | | | | | |
| 23** | | — | 67.8 | 68.0 | 8.3 | 8.0 | 10.8 | 10.1 |
| 24** | | 165 (—HCl) | 63.8 | 64.9 | 6.9 | 6.8 | 13.1 | 13.0 |
| 25 | | 265 | 76.9 | 70.2 | 7.2 | 7.2 | 15.8 | 13.7 |
| 26 | | 251 (—HCl) | 66.8 | 67.0 | 6.3 | 6.1 | 14.6 | 14.5 |
| 27 | | 251 | 76.5 | 73.3 | 6.8 | 6.5 | 16.7 | 17.7 |
| 28* | <50 (deliquesces) | 273 (—HCl) | 64.0 | 64.3 | 9.2 | 9.2 | 13.2 | 12.2 |
| 29 | 75–77 (deliquesces) | 315 (—HCl) | 68.3 | 67.3 | 9.7 | 9.5 | 11.9 | 11.1 |
| 30 | 55–70 (deliquesces) | 287 (—HCl) | 66.7 | 65.5 | 9.3 | 9.3 | 13.0 | 12.3 |
| 31 | 55–70 (deliquesces) | 273 (—HCl) | 65.9 | 66.3 | 9.1 | 9.2 | 13.6 | 13.1 |
| 32 | 147–149 | 246 (—HCl) | 63.9 | 63.4 | 8.6 | 8.3 | 14.9 | 15.0 |
| 33 | | 317 (—HCl) | 61.5 | 61.1 | 9.5 | 9.3 | 15.1 | 14.9 |
| 34 | | | 43.5 | 42.4 | 5.5 | 5.4 | 12.7 | 11.6 |
| 35 | | | 50.9 | 51.2 | 7.0 | 7.7 | 10.5 | 9.7 |
| 36 | | 176 | 41.1 | 41.1 | 5.0 | 5.2 | 11.1 | 11.0 |
| 37 | 29–50 (deliquesces) | | 62.8 | 61.5 | 8.3 | 8.5 | 15.7 | 13.8 |
| 38 | 116–118 | | 68.3 | 64.8 | 9.7 | 9.9 | 11.9 | 11.3 |
| 39 | 96–100 | | 68.2 | 66.5 | 9.7 | 9.4 | 11.9 | 10.9 |
| 40 | 115–120 | | 65.0 | 60.3 | 8.9 | 8.3 | 14.2 | 12.7 |
| 42 | 80–85 | | 68.9 | 66.0 | 9.9 | 9.8 | 11.5 | 11.0 |

*The elemental analysis data relates to the compound when containing ½ water molecule of crystallisation per molecule of compound.
**The elemental analysis data relates to the compound when containing 1 water molecule of crystallisation per molecule of compound.
***The elemental analysis data relates to the compound when containing 2 water molecules of crystallisation per molecule of compound.
****The elemental analysis data relates to the compound when containing 3 water molecules of crystallisation per molecule of compound.

EXAMPLE 8

The fungicidal activity of compounds of the invention was investigated by means of the following tests.

(a) Antisporulant Activity Against Vine Downy Mildew (*Plasmopara viticola*; PVA)

The test is a direct antisporulant one using a foliar spray. The lower surfaces of leaves of whole vine plants (cv Cabernet Sauvignon) are inoculated by spraying with an aqueous suspension containing $2.5 \times 10^4$ zoosporangia/ml 2 days prior to treatment with the test compound. The inoculated plants are kept for 24 hours in a high humidity compartment, then 24 hours at glasshouse ambient temperature and humidity. Infected leaves are sprayed on their lower surfaces with a solution of active material in 1:1 water/acetone containing 0.04% "TWEEN 20" (Trade Mark; a polyoxyethylene sorbitan ester surfactant). Plants are treated using an automated sprayline with an atomising nozzle. The concentration of the compound is 1000 ppm, and the spray volume is 700 l/ha. After spraying, the plants are returned to normal glasshouse conditions for 96 hours and are then transferred to the high humidity compartment for 24 hours to induce sporulation, prior to assessment. Assessment is based on the percentage of the leaf area covered by sporulation compared with that on control leaves.

(b) Direct Protectant Activity Against Vine Downy Mildew (*Plasmopara viticola*; PVP)

The test is a direct protectant one using a foliar spray. The lower surfaces of leaves of whole vine plants (cv Cabernet Sauvignon) are sprayed with the test compound at a dosage of 1000 ppm using an automated sprayline as described under (a), and after a subsequent period of 24 hours under normal glasshouse conditions the lower surfaces of the leaves are inoculated by spraying with an aqueous solution containing $2.5 \times 10^4$ zoosporangia/ml. The inoculated plants are kept for 24 hours in a high humidity compartment, 5 days under normal glasshouse conditions and then returned for a further 24 hours to high humidity. Assessment is based on the percentage of leaf area covered by sporulation compared with that on control leaves.

(c) Direct Protectant Activity Against Vine Grey Mould (*Botrytis cinerea;* BCP)

The test is a direct protectant one using a foliar spray. The lower surfaces of detached vine leaves (cv Cabernet Sauvignon) are sprayed with the test compound at a dosage of 1 kg/ha using a moving track sprayer. 24 hours after spraying the leaves are inoculated with droplets of aqueous suspension containing $10^5$ conidia/ml. After a further 5 days in high humidity the percentage of leaf area covered by disease is assessed.

(d) Direct Protectant Activity Against Broad Bean Grey Mould (*Botrytis cinerea;* BCB)

The test is a direct protectant one using a foliar spray. The upper surfaces of leaves of broad bean plants (cv The Sutton) are sprayed with the test compound at a dosage of 1000 ppm using an automated sprayline as described under (a). 24 hours after spraying the leaves are inoculated with an aqueous suspension containing $10^5$ conidia/ml. For 4 days after inoculation plants are kept moist in a humidity compartment at 21° C. Disease is assessed 4 days after inoculation, based on the percentage of leaf surface area covered by lesions.

(e) Activity Against Wheat Leafspot (*Leptosphaeria nodorum;* LN.)

The test is a direct therapeutic one, using a foliar spray. Leaves of wheat plants (cv Norman), at the single leaf stage, are inoculated by spraying with an aqueous suspension containing $1\times 10^6$ spores/mi. The inoculated plants are kept for 24 hours in a high humidity compartment prior to treatment. The plants are sprayed with a solution of the test compound at a dosage of 1000 ppm using an automated sprayline as described under (a). After drying, the plants are kept for 6-8 days at 22° C. and moderate humidity, followed by assessment. Assessment is based on the density of lesions per leaf compared with that on leaves of control plants.

(f) Activity Against Barley Powdery Mildew (*Erysiphe graminis* f.sp. hordei; EG)

The test is a direct therapeutic one, using a foliar spray. Leaves of barley seedlings, (cv. Golden Promise) are inoculated by dusting with mildew conidia one day prior to treatment with the test compound. The inoculated plants are kept overnight at glasshouse ambient temperature and humidity prior to treatment. The plants are sprayed with the test compound at a dosage of 1000 ppm using an automated sprayline as described under (a). After drying, plants are returned to a compartment at 20°-25° C. and moderate humidity for up to 7 days, followed by assessment. Assessment is based on the percentage of leaf area covered by sporulation compared with that on leaves of control plants.

(g) Activity Against Wheat Brown Rust (*Puccinia recondita;* PR)

The test is a direct protectant one using a foliar spray. Wheat seedlings (cv Avalon) are grown to the 1-1½ leaf stage. The plants are then sprayed with the test compound at a dosage of 1000 ppm using an automated sprayline as described under (a). Test compounds are applied as solutions or suspensions in a mixture of acetone and water (50:50 v/v) containing 0.04% surfactant ("TWEEN 20"- Trade Mark). 18-24 hours after treatment, the seedlings are inoculated by spraying the plants from all sides with an aqueous spore suspension containing about 10 spores/mi. For 18 hours after inoculation, the plants are kept in high humidity conditions at a temperature of 20°-22° C. Thereafter, the plants are kept in ambient glasshouse conditions, that is, in moderate relative humidity and at a temperature of 20° C. The disease is assessed 10 days after inoculation on the basis of the percentage of the plant covered by sporulating pustules compared with that on the control plants.

(h) Activity Against Rice Leaf Blast (*Pyricularia oryzae;* PO)

The test is a direct therapeutic one using a foliar spray. The leaves of rice seedlings (cv Aichiaishi—about 30 seedlings per pot) are sprayed with an aqueous suspension containing $10^5$ spores/ml 20-24 hours prior to treatment with the test compound. The inoculated plants are kept overnight in high humidity and then allowed to dry before spraying with the test compound at a dosage of 1000 ppm using an automated sprayline as described under (a). After treatment the plants are kept in a rice compartment at 25°-30° C. and high humidity. Assessments are made 4-5 days after treatment and are based on the density of necrotic lesions per leaf when compared with control plants.

(i) Activity Against Tomato Early Blight (*Alternaria solani;* AS)

This test measures the contact prophylactic activity of test compounds applied as a foliar spray. Tomato seedlings (cv Outdoor Girl) are grown to the stage at which the second true leaf is expanded. The plants are treated using an automated sprayline as described under (a). Test compounds are applied as solutions or suspensions in a mixture of acetone and water (50:50 v/v) containing 0.04% surfactant ("TWEEN 20"- Trade Mark). One day after treatment the seedlings are inoculated by spraying the leaf upper surfaces with a suspension of *A. solani* conidia containing $10^4$ spores/mi. For 4 days after inoculation plants are kept moist in a humidity compartment at 21° C. Disease is assessed 4 days after inoculation, based on the percentage of leaf surface area covered by lesions.

(j) Activity Against Wheat Eyespot in-vitro (*Pseudocercosporella herpotrichoides;* PHI)

This test measures the in vitro activity of compounds against the fungus causing wheat eyespot. The test compound is dissolved or suspended in acetone and is added to molten half strength Potato Dextrose Agar to give a final concentration of 100 ppm compound and 3.5% acetone. After agar has set, plates are inoculated with 6 mm diameter plugs of agar/mycelium taken from a 14 day old culture of *P. herpotrichoides.* Plates are incubated at 20° C. for 12 days and radial growth from the inoculation plug is measured.

(k) Activity Against Fusarium in-vitro (*Fusarium culmorum;* FSI)

This test measures the in vitro activity of compounds against a species of Fusarium that causes stem and root rots. The test compound is dissolved or suspended in acetone and added to molten half strength Potato Dextrose Agar to give a final concentration of 100 ppm compound and 3.5% acetone. After agar has set, plates are inoculated with 6 mm diameter plugs of agar and mycelium taken from a 7 day old culture of Fusarium sp. Plates are incubated at 20° C. for 5 days and radial growth from the plug is measured.

The extent of disease control in all the above tests is expressed as a rating compared with either an untreated control or a diluent-sprayed-control, according to the criteria:

0=less than 50% disease control
1=about 50-80% disease control
2=greater than 80% disease control The results of these tests are set out in Table II below:

TABLE II

| Compound Example No. | Fungicidal Activity | | | | | | | | | | |
|---|---|---|---|---|---|---|---|---|---|---|---|
| | PVA | PVP | BCP | BCB | LN | EG | PR | PO | AS | PHI | FSI |
| 1 |  | 1 |  |  |  | 2 | 2 |  |  | 1 | 1 |
| 2 |  |  |  |  |  | 1 |  |  |  |  |  |
| 3 |  | 1 |  | 2 |  |  | 1 |  |  |  |  |
| 4 | 1 | 2 |  |  |  | 2 | 2 |  |  |  | 1 |
| 5 |  |  | 2 |  | 1 | 2 | 2 |  |  | 1 | 1 |
| 6 |  | 1 |  |  |  |  |  |  |  |  |  |
| 7 | 1 | 1 |  |  |  | 1 |  |  |  |  |  |
| 8 |  | 1 |  |  |  | 1 |  |  |  |  | 1 |
| 9 |  | 1 |  |  |  | 1 |  |  | 2 |  |  |
| 10 |  |  |  |  |  | 1 |  |  |  |  |  |
| 11 |  | 1 |  |  |  |  |  |  | 1 |  | 1 |
| 12 |  | 2 |  |  |  |  |  |  | 2 |  | 1 |
| 13 |  | 2 |  |  |  |  |  |  |  |  |  |
| 14 | 1 | 2 |  |  |  | 1 |  |  | 1 |  |  |
| 15 | 1 | 2 |  |  |  | 1 | 1 |  |  |  |  |
| 16 |  | 2 |  | 1 | 1 | 2 | 2 |  |  |  | 1 |
| 17 | 1 |  |  |  |  |  |  |  |  |  |  |
| 18 |  |  |  |  |  |  |  |  | 1 | 1 | 1 |
| 19 |  | 1 |  |  |  |  |  |  |  |  | 1 |
| 20 |  | 1 |  |  |  |  |  |  |  |  |  |
| 21 |  | 1 |  |  |  |  |  |  |  |  |  |
| 22 |  | 2 |  |  |  | 1 |  |  |  |  |  |
| 23 |  |  |  |  |  | 1 | 1 |  |  |  | 1 |
| 32 |  | 2 |  |  | 1 | 2 | 1 |  |  |  |  |
| 33 |  |  |  |  |  | 1 | 1 |  |  |  | 1 |
| 34 |  | 1 |  | 1 |  |  |  |  | 1 |  |  |
| 36 |  |  |  | 1 |  | 1 |  |  | 1 |  |  |
| 37 |  |  |  |  |  | 1 | 1 |  |  |  |  |

We claim:

1. A compound of the formula I

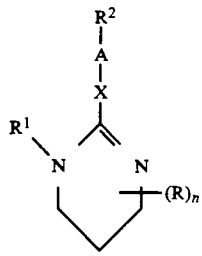

or an acid-addition salt or metal salt complex thereof in which n is 0, 1, 2 or 3;

R represents an optionally substituted alkyl, aryl or benzyl group;

$R^1$ represents a hydrogen atom or an optionally substituted alkyl or benzyl group;

$R^2$ represents an optionally substituted phenyl group; and

X represents a group —$NR^3$—$NR^3$— where each $R^3$ independently represents a hydrogen atom or an optionally substituted alkyl, aryl or benzyl group; and A represents a group —$(CR^6R^7)_m$— where m is 0, 1, 2, 3 or 4 and each of $R^6$ and $R^7$ is independently selected from a group consisting of hydrogen atoms and optionally substituted alkyl groups, optional substituents being selected from the group consisting of halogen atoms, nitro, cyano, hydroxyl, cycloalkyl, alkyl, haloalkyl, alkoxy, haloalkoxy, amino, alkylamino, dialkylamino, formyl, alkoxycarbonyl, carboxyl, alkanoyl, alkylthio, alkylsulphinyl, alkylsulphonyl, carbamoyl and alkylamido groups.

2. A fungicidal composition which comprises a carrier, and as an active ingredient, a fungicidally effective amount of the compound of formula I:

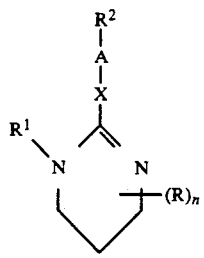

or an acid-addition salt or metal salt complex thereof in which n is 0, 1, 2 or 3;

R represents an optionally substituted alkyl, aryl or benzyl group;

$R^1$ represents a hydrogen atom or an optionally substituted alkyl or benzyl group;

$R^2$ represents an optionally substituted phenyl group; and

X represents a group —$NR^3$—$NR^3$— where each $R^3$ independently represents a hydrogen atom or an optionally substituted alkyl, aryl or benzyl group; and A represents a group —$(CR^6R^7)_m$— where m is 0, 1, 2, 3 or 4 and each of $R^6$ and $R^7$ is independently selected from a group consisting of hydrogen atoms and optionally substituted alkyl groups, optional substituents being selected from the group consisting of halogen atoms, nitro, cyano, hydroxyl, cycloalkyl, alkyl, haloalkyl, alkoxy, haloalkoxy, amino, alkylamino, dialkylamino, formyl, alkoxycarbonyl, carboxyl, alkanoyl, alkylthio, alkylsulphinyl, alkylsulphonyl, carbamoyl and alkylamido groups.

3. A composition according to claim 2 in which R represents a $C_1-C_6$ alkyl, phenyl or benzyl group, each group being optionally substituted by one or more substituents selected from halogen atoms, hydroxyl, $C_1-C_4$ alkyl, $C_1-C_4$ haloalkyl, $C_1-C_4$ alkoxy, $C_1-C_4$ haloalkoxy, amino, $C_1-C_4$ alkylamino, di-$C_1-C_4$ alkylamino, formyl, $C_1-C_4$ alkoxycarbonyl and carboxyl groups.

4. A composition according to claim 2 in which $R^1$ represents a hydrogen atom or a $C_1-C_6$ alkyl group optionally substituted by one or more substituents selected from halogen atoms, nitro, cyano, hydroxyl, $C_1-C_4$ alkyl, $C_1-C_4$ haloalkyl, $C_1-C_4$ alkoxy, $C_1-C_4$ haloalkoxy, amino, $C_1-C_4$ alkylamino, di-$C_1-C_4$ alkylamino, formyl, $C_1-C_4$ alkoxycabonyl and carboxyl groups.

5. A composition according to claim 1 in which $R^2$ represents a phenyl group optionally substituted by one or more substituents selected from halogen atoms, hydroxyl, $C_1-C_4$ alkyl, $C_1-C_4$ haloalkyl, $C_1-C_4$ alkoxy, $C_1-C_4$ haloalkoxy, amino, $C_1-C_4$ alkylamino, di-$C_1-C_4$ alkylamino, formyl, $C_1-C_4$ alkoxycarbonyl and carboxyl groups.

6. A composition according to claim 2 in which X represents a group $—NR^3—NR^3—$ where each $R^3$ independently represents a hydrogen atom or a $C_1-C_6$ alkyl group optionally substituted by one or more substituents selected from halogen atoms, hydroxyl, $C_1-C_4$ alkyl, $C_1-C_4$ haloalkyl, $C_1-C_4$ alkoxy, $C_1-C_4$ haloalkoxy, amino, $C_1-C_4$ alkylamino, di-$C_1-C_4$ alkylamino, formyl, $C_1-C_4$ alkoxycarbonyl and carboxyl groups.

7. A composition according to claim 2 in which A represents a group $—(CR^6R^7)_m—$ where m is 0, 1, 2, 3 or 4 and each of $R^6$ and $R^7$ is independently selected from a group consisting of hydrogen atoms and $C_1-C_6$ alkyl groups optionally substituted by one or more substituents selected from halogen atoms, hydroxyl, $C_1-C_4$ alkyl, $C_1-C_4$ haloalkyl, $C_1-C_4$ alkoxy, $C_1-C_4$ haloalkoxy, amino, $C_1-C_4$ alkylamino, di-$C_1-C_4$ alkylamino, formyl, $C_1-C_4$ alkoxycarbonyl and carboxyl groups.

8. A composition according to claim 2 in which n is 0, 1 or 2; R represents a methyl, phenyl, benzyl or butylbenzyl group; $R^1$ represents a hydrogen atoms; $R^2$ represents a phenyl, chlorophenyl, methylphenyl, propylphenyl or butylphenyl group; X represents a group $—NR^3—NR^3—$ where each $R^3$ represents a hydrogen atom or methyl group; and A represents a group $—(CR^6R^7)_m—$ where m is 0, 1, 2, 3 or 4 and each of $R^6$ and $R^7$ is independently selected from a group consisting of hydrogen atoms and methyl and ethyl groups.

9. A method of combatting fungus which comprises treating plants subject to or subjected to fungal attack, seeds of such plants or the medium in which such plants are growing or are to be grown with a fungicidally effective amount of a composition of claim 2.

10. A method of combatting fungus which comprises treating plants subject to or subjected to fungal attack, seeds of such plants or the medium in which such plants are growing or are to be grown with a fungicidally effective amount of a composition of claim 3.

* * * * *

UNITED STATES PATENT AND TRADEMARK OFFICE
CERTIFICATE OF CORRECTION

PATENT NO. : 5,332,745
DATED : July 26, 1994
INVENTOR(S) : PAUL A. CARTER ET AL.

It is certified that error appears in the above-identified patent and that said Letters Patent is hereby corrected as shown below:

Col. 23,

In claim 4, line 7 of the claim, "alkoxycabonyl" should read --alkoxycarbonyl--.

Col. 24,

In claim 8, line 3 of the claim, "atoms" should read --atom--.

In claim 10, line 5 of the claim, "claim 3" should read --claim 1--.

Signed and Sealed this

Fourteenth Day of March, 1995

Attest:

BRUCE LEHMAN

*Attesting Officer*     *Commissioner of Patents and Trademarks*